US008532751B2

(12) United States Patent
McKenna (10) Patent No.: US 8,532,751 B2
(45) Date of Patent: Sep. 10, 2013

(54) LASER SELF-MIXING SENSORS FOR BIOLOGICAL SENSING

(75) Inventor: Edward M. McKenna, Boulder, CO (US)

(73) Assignee: Covidien LP, Mansfield, MA (US)

( * ) Notice: Subject to any disclaimer, the term of this patent is extended or adjusted under 35 U.S.C. 154(b) by 984 days.

(21) Appl. No.: 12/242,738

(22) Filed: Sep. 30, 2008

(65) Prior Publication Data

US 2010/0081940 A1    Apr. 1, 2010

(51) Int. Cl.
*A61B 5/02* (2006.01)

(52) U.S. Cl.
USPC .......................................... 600/479; 600/504

(58) Field of Classification Search
USPC ............ 600/479, 438, 453–455, 504; 73/573
See application file for complete search history.

(56) References Cited

U.S. PATENT DOCUMENTS

| | | |
|---|---|---|
| 3,835,840 A | 9/1974 | Mount |
| 4,561,447 A | 12/1985 | Kawamura et al. |
| 4,676,253 A | 6/1987 | Newman et al. |
| 4,729,382 A | 3/1988 | Schaffer et al. |
| 4,830,017 A | 5/1989 | Perry et al. |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle et al. |
| 5,065,765 A | 11/1991 | Eckerle et al. |
| 5,103,831 A | 4/1992 | Niwa |
| 5,105,815 A | 4/1992 | Hall et al. |
| 5,119,824 A | 6/1992 | Niwa |
| 5,121,413 A | 6/1992 | Voegtly et al. |
| 5,131,400 A | 7/1992 | Harada et al. |
| 5,163,328 A | 11/1992 | Holland et al. |
| 5,170,796 A | 12/1992 | Kobayashi |
| 5,176,143 A | 1/1993 | Eckerle et al. |

(Continued)

FOREIGN PATENT DOCUMENTS

| | | |
|---|---|---|
| AU | 732799 | 8/1997 |
| CN | 1540314 | 10/2004 |

(Continued)

OTHER PUBLICATIONS

Nilsson, G.E. et al, Laser Doppler Perfusion Monitoring and Imaging, Biomedical Photonics Handbook, edited by Tuan, Vo-Dinh, Chapter 15, pp. 1-24, (2003).*

(Continued)

*Primary Examiner* — Unsu Jung
*Assistant Examiner* — Daniel Huntley
(74) *Attorney, Agent, or Firm* — Shvarts & Leiz LLP (57) ABSTRACT

According to embodiments, systems, devices, and methods for biological sensing with laser self-mixing sensors are disclosed. In one embodiment, one or more self-mixed laser Doppler signals may be used to detect blood flow velocity or blood vessel wall velocity. In one embodiment, a blood vessel wall compliance may be derived from the blood vessel wall velocity. In one embodiment, blood pressure may be calculated based at least in part on blood flow velocity or based at least in part on blood flow velocity and blood vessel compliance. In one embodiment, common mode noise may be removed from one or more laser signals.

31 Claims, 7 Drawing Sheets

(56) References Cited

U.S. PATENT DOCUMENTS

| | | |
|---|---|---|
| 5,178,154 A | 1/1993 | Ackmann et al. |
| 5,179,956 A | 1/1993 | Harada et al. |
| 5,204,922 A | 4/1993 | Weir et al. |
| 5,238,000 A | 8/1993 | Niwa |
| 5,239,185 A | 8/1993 | Ito et al. |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,299,570 A | 4/1994 | Hatschek |
| 5,309,917 A | 5/1994 | Wang et al. |
| 5,413,100 A | 5/1995 | Barthelemy et al. |
| 5,431,159 A | 7/1995 | Baker et al. |
| 5,450,852 A | 9/1995 | Archibald et al. |
| 5,467,771 A | 11/1995 | Narimatsu et al. |
| 5,490,506 A | 2/1996 | Takatani et al. |
| 5,494,043 A | 2/1996 | O'Sullivan et al. |
| 5,497,779 A | 3/1996 | Takaya et al. |
| 5,505,209 A | 4/1996 | Reining |
| 5,533,511 A | 7/1996 | Kaspari et al. |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan et al. |
| 5,575,285 A | 11/1996 | Takanashi et al. |
| 5,596,986 A | 1/1997 | Goldfarb |
| 5,617,868 A | 4/1997 | Harada et al. |
| 5,632,273 A | 5/1997 | Suzuki |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa et al. |
| 5,682,898 A | 11/1997 | Aung et al. |
| 5,685,316 A | 11/1997 | Schookin et al. |
| 5,704,362 A | 1/1998 | Hersh et al. |
| 5,709,212 A | 1/1998 | Sugo et al. |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu et al. |
| 5,766,127 A | 6/1998 | Pologe et al. |
| 5,772,601 A | 6/1998 | Oka et al. |
| 5,772,602 A | 6/1998 | Sakai et al. |
| 5,776,071 A | 7/1998 | Inukai et al. |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,827,181 A | 10/1998 | Dias et al. |
| 5,830,131 A | 11/1998 | Caro et al. |
| 5,832,924 A | 11/1998 | Archibald et al. |
| 5,833,618 A | 11/1998 | Caro et al. |
| 5,848,970 A | 12/1998 | Voss et al. |
| 5,851,178 A | 12/1998 | Aronow |
| 5,857,975 A | 1/1999 | Golub |
| 5,873,834 A | 2/1999 | Yanagi et al. |
| 5,891,022 A | 4/1999 | Pologe |
| 5,904,654 A | 5/1999 | Wohltmann et al. |
| 5,941,828 A | 8/1999 | Archibald et al. |
| 5,964,711 A | 10/1999 | Voss et al. |
| 5,983,122 A | 11/1999 | Jarman et al. |
| 6,002,952 A | 12/1999 | Diab et al. |
| 6,004,274 A | 12/1999 | Nolan et al. |
| 6,007,492 A | 12/1999 | Goto et al. |
| 6,011,986 A | 1/2000 | Diab et al. |
| 6,022,320 A | 2/2000 | Ogura et al. |
| 6,026,312 A | 2/2000 | Shemwell et al. |
| 6,027,452 A | 2/2000 | Flaherty et al. |
| 6,027,453 A | 2/2000 | Miwa et al. |
| 6,027,455 A | 2/2000 | Inukai et al. |
| 6,031,603 A | 2/2000 | Fine et al. |
| 6,045,509 A | 4/2000 | Caro et al. |
| 6,064,898 A | 5/2000 | Aldrich |
| 6,067,462 A | 5/2000 | Diab et al. |
| 6,083,171 A | 7/2000 | Ono et al. |
| 6,095,974 A | 8/2000 | Shemwell et al. |
| 6,095,987 A | 8/2000 | Shmulewitz et al. |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,253,097 B1 | 6/2001 | Aronow et al. |
| 6,263,222 B1 | 7/2001 | Diab et al. |
| 6,292,689 B1 | 9/2001 | Wallace et al. |
| 6,293,915 B1 | 9/2001 | Amano et al. |
| 6,299,582 B1 | 10/2001 | Brockway et al. |
| 6,332,867 B1 | 12/2001 | Chen et al. |
| 6,350,242 B1 | 2/2002 | Doten et al. |
| 6,371,921 B1 | 4/2002 | Caro et al. |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura et al. |
| 6,589,185 B1 | 7/2003 | Archibald et al. |
| 6,594,513 B1 | 7/2003 | Jobsis et al. |
| 6,602,199 B2 | 8/2003 | Chen et al. |
| 6,602,201 B1 | 8/2003 | Heep et al. |
| 6,606,511 B1 | 8/2003 | Ali et al. |
| 6,615,064 B1 | 9/2003 | Aldrich |
| 6,626,839 B2 | 9/2003 | Doten et al. |
| 6,631,281 B1 | 10/2003 | Kastle |
| 6,645,156 B2 | 11/2003 | Oka |
| 6,647,279 B2 | 11/2003 | Pologe |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab et al. |
| 6,707,257 B2 | 3/2004 | Norris |
| 6,754,515 B1 | 6/2004 | Pologe |
| 6,767,328 B2 | 7/2004 | Kulik |
| 6,773,397 B2 | 8/2004 | Kelly |
| 6,783,498 B2 | 8/2004 | Sackner et al. |
| 6,816,741 B2 | 11/2004 | Diab |
| 6,822,564 B2 | 11/2004 | Al-Ali |
| 6,825,619 B2 | 11/2004 | Norris |
| 6,826,419 B2 | 11/2004 | Diab et al. |
| 6,827,688 B2 | 12/2004 | Goto et al. |
| 6,831,741 B1 | 12/2004 | De Kruif et al. |
| 6,852,083 B2 | 2/2005 | Caro et al. |
| 6,855,112 B2 | 2/2005 | Kao et al. |
| 6,863,652 B2 | 3/2005 | Huang et al. |
| 6,869,403 B2 | 3/2005 | Narimatsu et al. |
| 6,929,610 B2 | 8/2005 | Forstner |
| 6,996,427 B2 | 2/2006 | Ali et al. |
| 7,004,907 B2 | 2/2006 | Banet et al. |
| 7,043,293 B1 | 5/2006 | Baura |
| 7,044,918 B2 | 5/2006 | Diab |
| 7,047,054 B2 | 5/2006 | Benni |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,107,116 B2 | 9/2006 | Geng |
| 7,184,809 B1 | 2/2007 | Sterling et al. |
| 7,215,984 B2 | 5/2007 | Diab et al. |
| 7,215,986 B2 | 5/2007 | Diab et al. |

| | | | |
|---|---|---|---|
| 7,242,997 | B2 | 7/2007 | Geng |
| 7,251,518 | B2 | 7/2007 | Herrmann |
| 7,252,636 | B2 | 8/2007 | Brown |
| 7,283,242 | B2 | 10/2007 | Thornton |
| 7,313,427 | B2 | 12/2007 | Benni |
| 7,320,030 | B2 | 1/2008 | Brown |
| 7,330,746 | B2 | 2/2008 | Demuth et al. |
| 7,335,162 | B2 | 2/2008 | Eide |
| 7,376,238 | B1 | 5/2008 | Rivas et al. |
| 7,390,300 | B2 | 6/2008 | Inukai et al. |
| 7,390,301 | B2 | 6/2008 | Skrabal et al. |
| 7,393,327 | B2 | 7/2008 | Inukai et al. |
| 7,400,257 | B2 | 7/2008 | Rivas |
| 7,455,643 | B1 | 11/2008 | Li et al. |
| 7,481,772 | B2 | 1/2009 | Banet |
| 7,485,095 | B2 | 2/2009 | Shusterman |
| 2002/0068859 | A1 | 6/2002 | Knopp |
| 2003/0149371 | A1 | 8/2003 | Shiga et al. |
| 2005/0148885 | A1 | 7/2005 | Tweed et al. |
| 2005/0251344 | A1 | 11/2005 | Appel et al. |
| 2005/0261594 | A1 | 11/2005 | Banet |
| 2005/0267346 | A1 | 12/2005 | Faber et al. |
| 2006/0009700 | A1 | 1/2006 | Brumfield et al. |
| 2006/0058690 | A1 | 3/2006 | Bartnik et al. |
| 2006/0063992 | A1 | 3/2006 | Yu et al. |
| 2006/0063993 | A1 | 3/2006 | Yu et al. |
| 2006/0079945 | A1 | 4/2006 | Libbus |
| 2006/0206021 | A1 | 9/2006 | Diab |
| 2006/0217614 | A1 | 9/2006 | Takala et al. |
| 2006/0217628 | A1 | 9/2006 | Huiku |
| 2006/0241975 | A1 | 10/2006 | Brown |
| 2006/0285736 | A1 | 12/2006 | Brown |
| 2006/0287603 | A1 | 12/2006 | Bartnik et al. |
| 2007/0016096 | A1 | 1/2007 | McNabb |
| 2007/0066910 | A1 | 3/2007 | Inukai et al. |
| 2007/0083093 | A1 | 4/2007 | Diab |
| 2007/0118045 | A1 | 5/2007 | Naghavi et al. |
| 2007/0225582 | A1 | 9/2007 | Diab et al. |
| 2007/0249467 | A1 | 10/2007 | Hong et al. |
| 2008/0015451 | A1 | 1/2008 | Hatib et al. |
| 2008/0030468 | A1 | 2/2008 | Ali et al. |
| 2008/0033305 | A1 | 2/2008 | Hatib et al. |
| 2008/0132798 | A1 | 6/2008 | Hong et al. |
| 2008/0214903 | A1 | 9/2008 | Orbach |
| 2008/0214942 | A1 | 9/2008 | Oh et al. |
| 2008/0242955 | A1 | 10/2008 | Uutela et al. |
| 2009/0048497 | A1 | 2/2009 | Keren |
| 2009/0318908 | A1* | 12/2009 | Van Pieterson et al. ......... 606/9 |

FOREIGN PATENT DOCUMENTS

| | | |
|---|---|---|
| CN | 2691489 | 4/2005 |
| CN | 1223843 | 10/2005 |
| CN | 11080192 | 11/2007 |
| DE | 19640807 | 9/1997 |
| EP | 0443267 | 8/1991 |
| EP | 702931 | 3/1996 |
| EP | 0755221 | 1/1997 |
| EP | 793942 | 9/1997 |
| GB | 2356250 | 5/2001 |
| GB | 2356251 | 5/2001 |
| GB | 2356252 | 5/2001 |
| JP | 03231630 | 10/1991 |
| JP | 06142082 | 5/1994 |
| JP | 07136136 | 5/1995 |
| JP | 24337605 | 12/2004 |
| JP | 25095581 | 4/2005 |
| JP | 26075354 | 3/2006 |
| JP | 26081703 | 3/2006 |
| JP | 26239267 | 9/2006 |
| JP | 26297125 | 11/2006 |
| JP | 26326153 | 12/2006 |
| JP | 3939782 | 7/2007 |
| JP | 3944448 | 7/2007 |
| JP | 27196001 | 8/2007 |
| JP | 27259918 | 10/2007 |
| JP | 4038280 | 1/2008 |
| MX | PA02011937 | 4/2003 |
| WO | WO-9749330 | 12/1997 |
| WO | WO-2007105175 | 9/2007 |

OTHER PUBLICATIONS de Mul, F.F.M., et al, Self-Mixing laser-Doppler velocimetry of liquid flow and of blood perfusion in tissue, Applied Optics, 31(27), pp. 5844-5851, (1992).*

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Giuliani, Guido, Norgia, Michele, Donati, Silvano, Bosch, Thierry, "Laser diode self-mixing technique for sensing applications," J. Opt. A Pure Appl. Opt. 4 (2002) S283-S294.

Hast, Jukka, Myllyla, Risto, Sorvoja, Hannu, Nissila, Seppo, "Arterial compliance measurement using a non-invasive laser Doppler measurement system," Optical Techniques and Instrumentation for the Measurement of Blood Composition, Structure and Dynamics, Proceedings of SPIE, vol. 4163 (2000); pp. 24-32.

Marque, Valérie, Van Essen, Helma, Struijker-Boudier, Harry A.J., Atkinson, Jeffrey, Lartaud-Idjouadiene, Isabelle, "Determination of Aortic Elastic Modulus by Pulse Wave Velocity and Wall Tracking in a Rat Model of Aortic Stiffness," J. Vas Res 2001; 38:546-550.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Plantier, Guy, Bes, Caroline, Bosch Thierry, "Behavioral Model of a Self-Mixing Laser Diode Sensor," IEEE Journal of Quantum Electronics, vol. 41, No. 9, Sep. 2005; pp. 1157-1167.

Scalise, Lorenzo, Steenbergen, Wiendelt, De Mul, Frits, "Self-Mixing feedback in a laser diode for intra-arterial optical blood velocimetry," Applied Optics, vol. 40, No. 25, Sep. 2001; pp. 4608-4615.

Scalise, Lorenzo, Yu, Yanguang, Giuliani, Guido, "Self-Mixing Laser Diode Velocimetry: Application to Vibration and Velocity Measurement," IEEE Transactions on Instrumentation and Measurement, vol. 53, No. 1, Feb. 2004; pp. 223-232.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

Yu, Yanguang, Ye, Huiying, Yao, Jianquan, "Analysis for the self-mixing interference effects in a laser diode at high optical feedback levels," J. Opt. Pure Appl. Opt. 5 (2003) 117-122.

Wei, Lu, Chicharo, Joe, Yu, Yanguang, Xi, Jiangtao, "Pre-Processing of Signals Observed from Laser Diode Self-mixing Intereferometries Using Neural Networks," IEEE International Symposium on Intelligent Signal Processing WISP Oct. 3-5, 2007, 1-5.

* cited by examiner

LASER SELF-MIXING SENSORS FOR BIOLOGICAL SENSING

SUMMARY

The present disclosure is directed to a method for the noninvasive monitoring of blood related measurements, such as blood pressure, with self-mixed laser Doppler signals. In one embodiment, the method comprises receiving a first self-mixed laser Doppler signal which at least partially represents the movement of blood within a blood vessel. The velocity of the blood flow within the blood vessel is at least partially derived from the first self-mixed laser Doppler signal. A blood pressure measurement may then be calculated at least in part from the derived blood velocity. In one embodiment, the method comprises receiving a second self-mixed laser Doppler signal which at least partially represents the movement of blood vessel walls. The compliance of the blood vessel is at least partially derived from the second self-mixed laser Doppler signal. In one embodiment, the method comprises receiving at least two self-mixed laser Doppler signals, the first of which at least partially represents the movement of blood within a blood vessel and the second of which at least partially represents the movement of blood vessel walls. The velocity of the blood flow within the vessel is at least partially derived from the first self-mixed laser Doppler signal, and the compliance of a blood vessel is at least partially derived from the second self-mixed laser Doppler signal. A blood pressure measurement may be calculated from the derived blood velocity and derived blood vessel compliance.

In one embodiment, a first laser is configured to penetrate within a blood vessel, and a second laser is configured to penetrate to a blood vessel wall. This may be done by selecting different and suitable wavelengths of the first and second lasers. For example, the wavelength of the first laser may be selected so that it can penetrate into a blood vessel, whereas the wavelength of the second laser may be selected so that it can only penetrate to the wall of a blood vessel.

In one embodiment, the received first and second self-mixed laser Doppler signals may be converted into a first and second electric signals. In one embodiment, common-mode noise may be removed from the first, the second, or the first and second electric signals.

In one embodiment, the electric signals may be converted into frequency spectra. Doppler frequency shifts may then be derived from these spectra, which may then allow derivation of a velocity. For example, the first self-mixed laser Doppler electric signal may be converted into a first frequency spectrum, and a first Doppler frequency shift may be derived from this spectrum. A blood flow velocity may then be derived at least partially from this first Doppler frequency shift. As another example, the same process may be used for the second self-mixed laser Doppler electric signal to result in a blood vessel wall velocity. In one embodiment, blood flow velocity may also be derived in part from the second self-mixed laser Doppler electric signal. In one embodiment, blood vessel wall velocity may also be derived in part from the first self-mixed laser Doppler electric signal. In one embodiment, the blood vessel wall velocity may then be used to derive a blood vessel compliance. In one embodiment, blood pressure is calculated from the derived blood flow velocity. In another embodiment, blood pressure is calculated from the derived blood flow velocity and blood vessel compliance.

BRIEF DESCRIPTION OF THE DRAWINGS

The above and other features of the disclosure, its nature and various advantages will be more apparent upon consideration of the following detailed description, taken in conjunction with the accompanying drawings in which.

DETAILED DESCRIPTION

Laser Doppler measurement is a method that may be used for determining velocity. When a laser beam is incident on an object moving at least partially in the axis of the laser beam, any laser reflections back toward the laser source will experience a shift in frequency. This frequency shift is known as the Doppler shift, and is commonly exhibited in the drop in apparent frequency of a siren as the siren moves past the observer. For the case of a laser beam incident on a moving object, if the object is moving toward the laser source, any laser reflections from the object directed toward the laser source will have a higher frequency than the original laser beam. Likewise, if the object is moving away from the laser source, laser reflections from the object directed toward the laser source will have a lower frequency than the original laser beam. By comparing the reflected laser frequency with the original laser frequency, measurements of the velocity of the moving object can be made.

A common technique for the frequency comparison of an original laser signal and a reflected laser signal is interferometry, which involves the superposition or mixing of the original laser signal and the reflected laser signal. Many laser interferometers, such as the well-known Michelson interferometer, rely on splitting the original laser beam into two, using one for the measurement of interest, and mixing the other beam with the reflected measurement beam. This type of setup involves the use of beam splitting and recombining optics, which can be bulky and unwieldy. In addition, exacting and painstaking calibrations must be made to assure that the various beam paths are precisely aligned.

Another method for interferometric measurements is to use a self-mixing process. In a self-mixing process, instead of mixing the reflected laser with a beam split from the original laser, some portion of the reflected laser can be allowed into the laser cavity. Within the laser cavity, the reflected laser will mix with the original laser, and the newly resulting laser waveform can be detected. This is termed self-mixing because the reflected signal is mixed directly with the original laser, thus actually changing the original laser characteristic.

Figure 1:
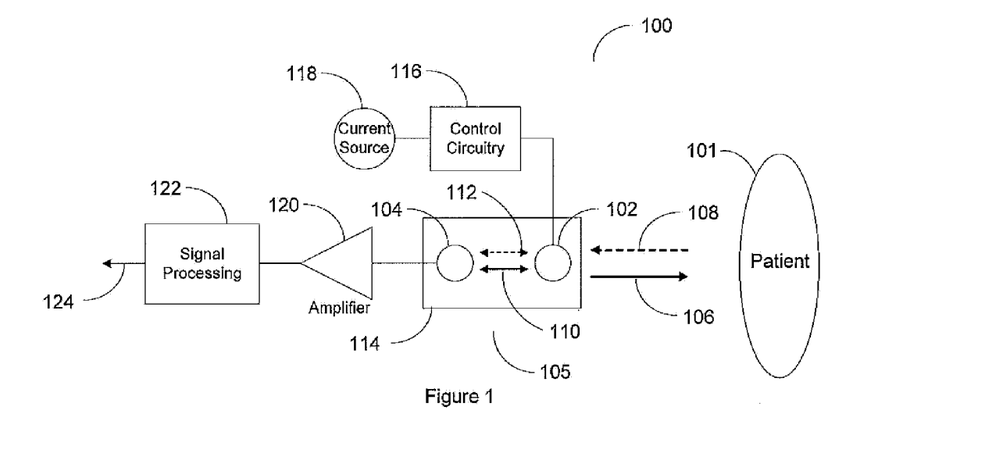
FIG. 1 shows an illustrative self-mixed laser sensor in accordance with an embodiment.

FIG. 1 depicts an illustrative self-mixed laser sensor 100 for medical applications. In one embodiment, the laser sensor is a laser diode package, 105, which comprises a laser emitter diode, 102, and a monitor photodiode, 104, within a laser cavity, 114. The laser emitter diode 102 is the actual lasing element in the diode package, and can emit a laser beam 106 that can be used for velocity measurement purposes, for example in a patient 101. Some portion 112 of the reflected laser beam 108 can be allowed back into the laser cavity 114, where it self-mixes with the original laser signal 110 that is also within the cavity. The monitor photodiode 104 can then sense the mixed laser signal, typically converting light amplitude into an electric signal, which may then boosted by an amplifier 120 and sent to a signal processing unit 122, resulting in a final electric signal 124. An electric signal may comprise a voltage or a current signal. The laser emitter diode 102 may be powered by a current source 118 that is modulated by control circuitry 116.

Figure 2:
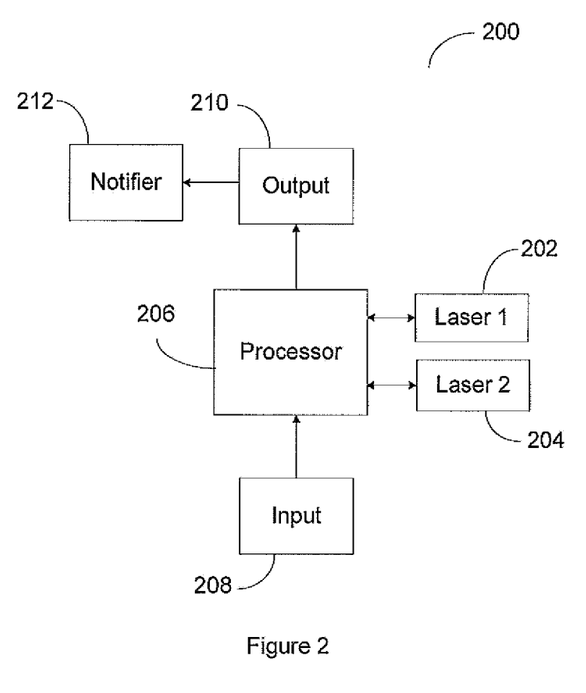
FIG. 2 is a block diagram of a blood pressure measurement system incorporating two self-mixed laser sensors in accordance with an embodiment.

FIG. 2 depicts a block diagram of an exemplary device 200 that may be used to measure, for example, blood pressure. Two self-mixed laser sensors as described in FIG. 1, 202 and 204, are coupled to a processor 206. The processor 206 may receive data from an input 208, and send data to an output 210. The processor 206 may also send or receive data to and from memory. The output 210 may be further coupled to a notifier 212. Laser sensors 202 and 204 may emit at different wavelengths. In one embodiment (not pictured), the device may only comprise a single self-mixed laser sensor as described in FIG. 1.

Processor 206 receives electric signals corresponding to laser measurements from laser sensors 202 and 204. Processor 206 may, in some embodiments transform the electric signals into the frequency domain, by means of a transformation such as a fast Fourier transform (FFT). Processor 206 may send control signals to the laser sensors 202 and 204, to control the control circuitry 116 linked to the laser emitter diode 102, the current source 118, the amplifier 120, or the signal processing unit 122. Processor 206 may contain a filter, which may allow electronic filtration processes such as common-mode noise removal. Processor 206 may receive data from input 208, which may be a user interface through which a user may be able to specify parameters relevant to the measurement process, such as sampling modes or sampling times. Processor 206 may be a processor from, for example, the ARM11 family of processors. The data that processor 206 receives, either from the input 208 or from the laser sensors 202 and 204, may be stored in memory. The memory may also store data or signals that processor 206 has processed, as well as data that the processor 206 will send to output, 210. Input 208 may also be any other means by which instructions for the processor may be stored or generated, such as a memory device or a network. Processor 206 may send data to an output 210, which may be a graphical display unit capable of presenting data to a user. Output 210 may also comprise memory that can store the data received from processor 206, as well as any other means by which data may be stored, presented, or further processed. A notifier 212 may be coupled to output 210. Notifier 212 may be capable of generating an auditory, visual, or other signal for notification purposes, depending on certain criteria such as laser signal strength. In one embodiment, notifier 212 may emit an audible tone whose volume is directly proportional to the electric signals received from one or both of the laser sensors 202 and 204. In one embodiment, the overall volume of the audible tone may be a function of the electric signal received from sensor 202 and the electric signal received from sensor 204 at a particular time. The overall volume of the audible tone may be dependent on the sum, product, or other mathematical combination of the amplitudes of the electric signals from sensor 202 and 204. For example, as laser sensors 202 and 204 are moved so that the mixed laser signal amplitude measured by the monitor photodiodes 104 present in both laser sensors 202 and 204 increases, the audible tone emitted by the notifier 212 may increase in volume. As the sensors 202 and 204 are moved so that the measured laser signal amplitude decreases, the audible tone volume may decrease. The notifier 212 may be a buzzer, alarm, or some other device that provides an audible or visible notification.

Figure 3:
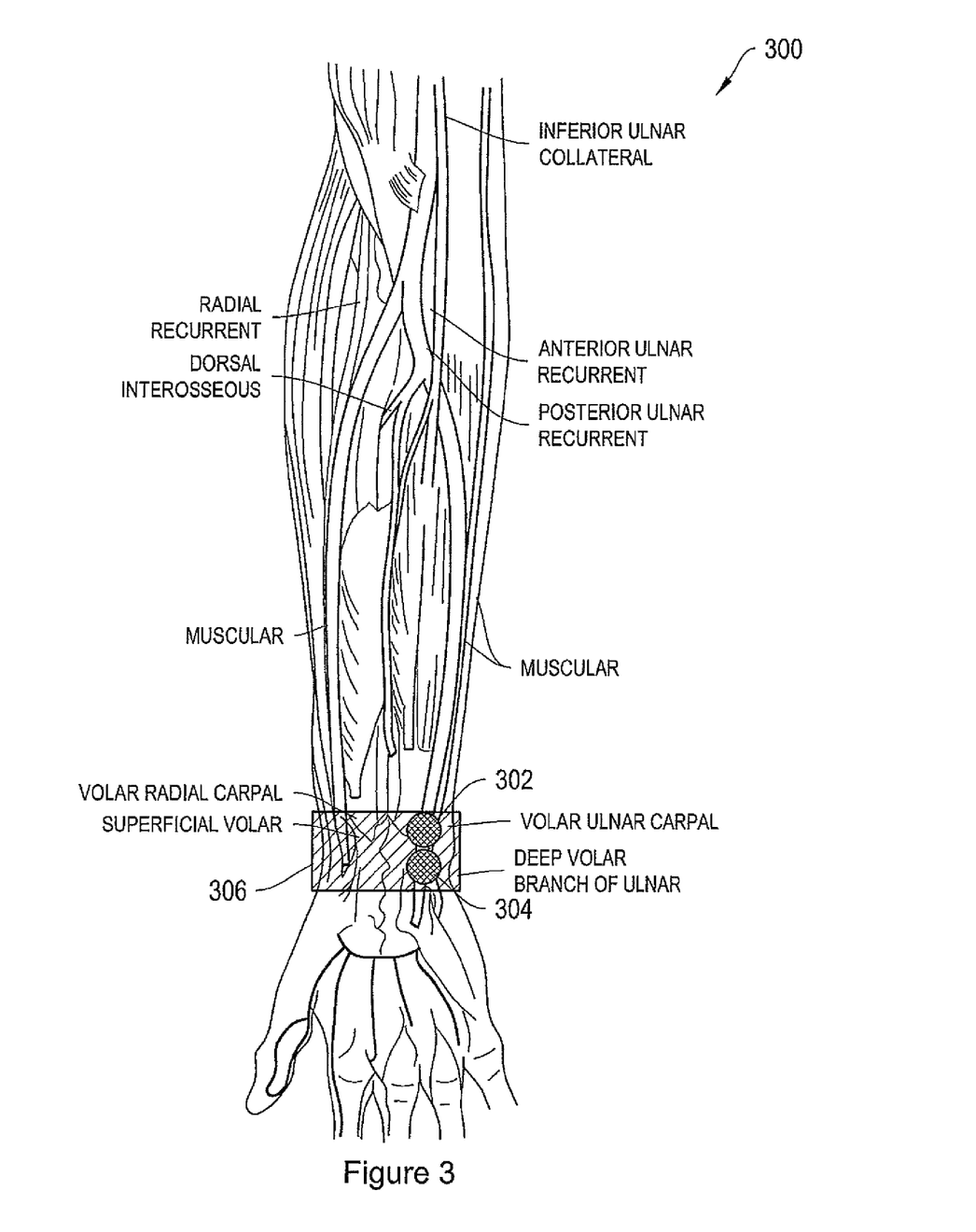
FIG. 3 shows an illustrative view of a support structure integrating self-mixed laser sensors coupled with a patient in accordance with an embodiment.

FIG. 3 shows an illustrative view of an exemplary support structure 306, in this example a wristband, integrating two laser sensors 302 and 304. The laser sensors 302 and 304 may, as for laser sensors 202 and 204, emit light at different wavelengths. Laser sensors 302 and 304 may be fastened or secured to support structure 306 in a permanent or temporary fashion. For example, laser sensors 302 and 304 may be directly integrated into the support structure 306 and may not be removable. The sensors 302 and 304 may also be secured to the structure 306 with suitable fasteners. The support structure 306 may be a flexible or rigid band that may fit around the extremity of a patient. The support structure 306 may include fasteners and/or may be stretchable or deformable, allowing the structure 306 to be secured in a suitable configuration for measurement purposes. The exemplary illustration 300 depicts a possible configuration for the support structure 306 and laser sensors 302 and 304. In one embodiment (not pictured), the support structure 306 may only comprise one laser sensor.

Figure 4:
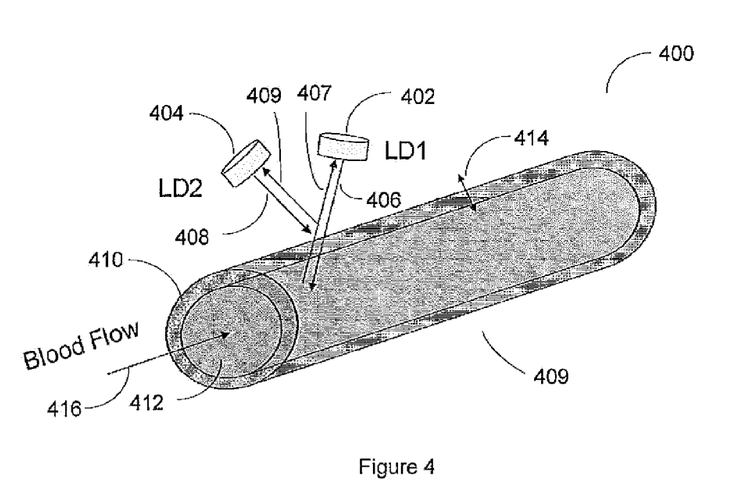
FIG. 4 illustrates the coupling of two self-mixed laser sensors with a blood vessel in accordance with an embodiment.

FIG. 4 illustrates the exemplary coupling of two laser sensors 402 and 404 with an artery 409 comprised of a blood vessel wall 410 and blood 412. The flow of blood 412 occurs in the direction indicated by 416, and the arterial wall 410 moves in the directions indicated by 414. Laser sensors 402 and 404 may emit lasers of different wavelengths; for example, the laser 406 emitted from laser sensor 402 may be of a wavelength that allows penetration of the arterial wall 410 into the blood 412, whereas the laser 408 emitted from laser sensor 404 may be of a different wavelength that does not allow penetration through the blood vessel wall 410. By selecting the penetration depth of a particular laser, the degree to which it couples to either the blood flow or the arterial wall may be controlled. For example, a first laser that penetrates to a greater depth than a second laser may couple more strongly to the blood flow than the second laser. However, both lasers may still each couple to both the blood flow and the arterial wall to differing degrees. Consequently, in one embodiment, a single self-mixed laser sensor may be used to determine blood velocity, arterial compliance, and blood pressure. The laser reflections 407 and 409 may have frequencies that are Doppler shifted due to the movement of blood 412 and arterial wall 410. When the laser reflections 407 and 409 are allowed to reenter the laser cavity, self-mixing will result in the laser signal in the cavity having amplitude fluctuations with a frequency equal to the Doppler shift of the laser reflections. In one embodiment, laser sensor 402 may be oriented so that the optical symmetry axis of the laser it emits is not perpendicular to the blood flow direction in the blood vessel.

Figure 5:
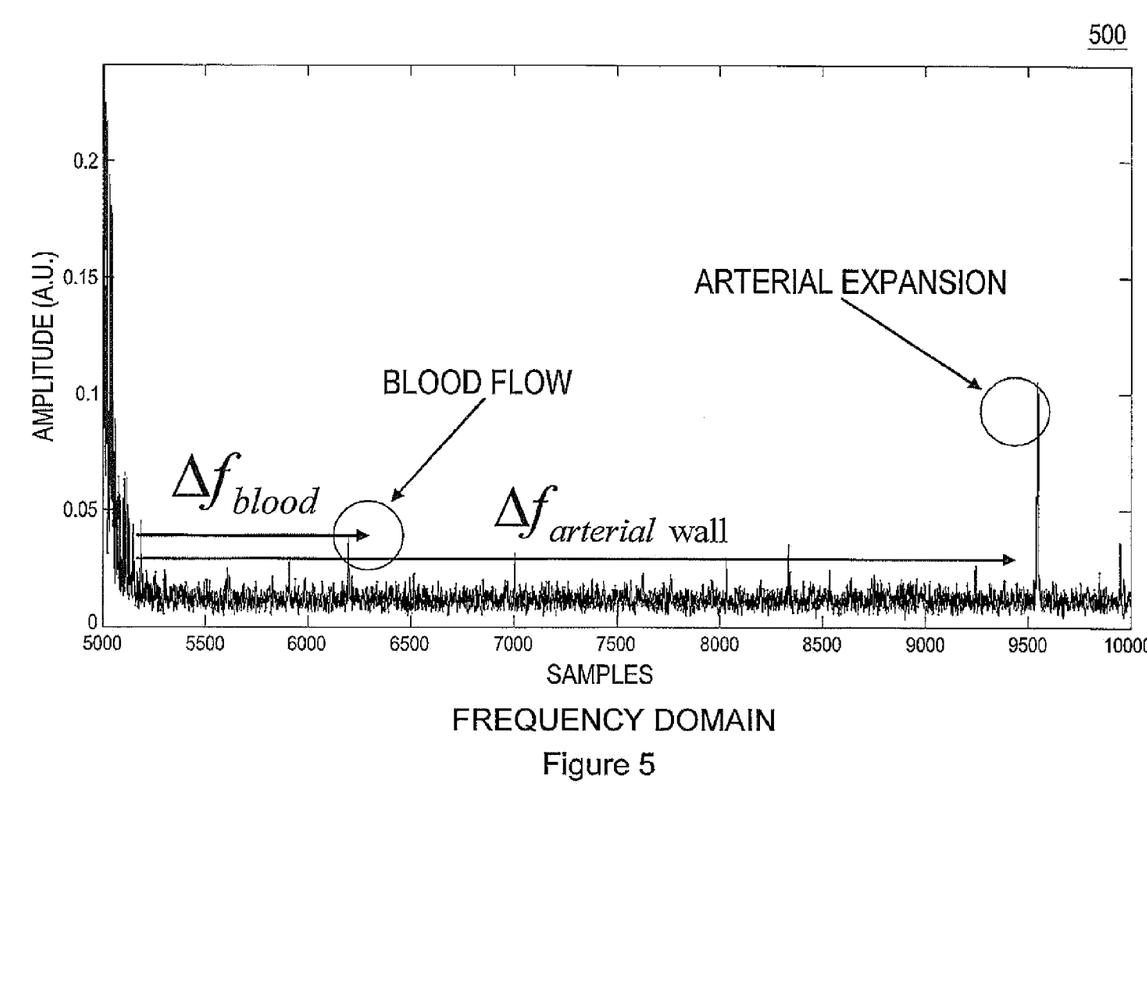
FIG. 5 shows an illustrative frequency spectrum for determining frequency shifts in accordance with an embodiment.

FIG. 5 shows an exemplary frequency spectrum 500 that may be derived from self-mixed laser Doppler measurements of blood flow velocity and arterial wall velocity. The cavity laser signal with amplitude fluctuations occurring at the Doppler shift frequency is observed by the monitor photodiode 104, which converts the light signal into an electric signal 124 with amplitude values proportional to the light signal amplitude. The electric signal 124 may be transformed into the frequency domain by the processor 206. This may be accomplished by methods such as a fast Fourier transform (FFT) or any other time-domain to frequency-domain transformation. The exemplary frequency spectrum 500 shown in FIG. 5 depicts the frequency-domain data that may be collected from two laser sensors 402 and 404. The Doppler frequency shift can be described as:

$$\Delta f = \frac{2nv(\cos\theta)}{\lambda} \quad (1)$$

where Δf, n, v, θ, and λ are the Doppler frequency shift, the refractive index, velocity of the object, the angle between the velocity vector of the object and the laser axis, and the wavelength of the laser in vacuum, respectively. The specific Doppler frequency shifts for blood velocity or arterial wall velocity may be determined by first selecting the frequency range in which the blood or arterial wall velocity is to be found and then selecting the peak with the highest amplitude in that frequency range. In one embodiment, the Doppler frequency shifts for blood velocity or arterial wall velocity may be identified by learning-based algorithms trained with clinical data. In one embodiment, these algorithms and clinical data may be stored in a memory. In one embodiment, the Doppler frequency shifts for both blood velocity and arterial wall velocity may be present in a laser signal. The degree of coupling of the laser signal to blood velocity or arterial wall velocity may be reflected by the relative amplitudes of the frequency peaks representing the blood velocity or arterial wall velocity in the same or different frequency spectrums. For example, if the first laser signal couples more strongly to blood velocity than to arterial wall velocity compared to the second laser signal, then the ratio of the amplitude of the blood velocity peak to the amplitude of the arterial wall velocity peak in the frequency spectrum of the first laser signal may be larger than the ratio of the amplitude of the blood velocity peak to the amplitude of the arterial wall velocity peak in the frequency spectrum of the second laser signal. Likewise, if the second laser signal couples more strongly to arterial wall velocity than to blood velocity compared to the first laser signal, then the ratio of the amplitude of the arterial wall velocity peak to the amplitude of the blood velocity peak in the frequency spectrum of the second laser signal may be larger than the ratio of the amplitude of the arterial wall velocity peak to the amplitude of the blood velocity peak in the frequency spectrum of the first laser signal. In one embodiment, the specific Doppler frequency shifts for blood velocity or arterial wall velocity may be determined from two laser signals, for example laser reflections 407 and 409. In one embodiment, the specific Doppler frequency shifts for blood velocity or arterial wall velocity may be determined from one laser signal. The specific Doppler frequency shifts for blood velocity or arterial wall velocity, once determined, may be used to calculate blood velocity or arterial wall velocity via equation (1). In one embodiment, the frequency range in which blood flow or arterial wall velocity can be found may be derived by using previously-known minimum and maximum values of blood flow or arterial wall velocity, converting the minimum and maximum values to Doppler frequency shift equivalents via equation (1), then using the Doppler shift equivalents to define the frequency range. In another embodiment, the minimum and maximum values of arterial wall velocity may be derived by converting previously known minimum and maximum values of arterial compliance into minimum and maximum values of arterial wall velocity. This conversion may be done by using the following equation:

$$C = \frac{\Delta V}{\Delta P} \quad (2)$$

where C, ΔV, and ΔP are the compliance, the change in volume, and the change in pressure, respectively. The change in volume may be calculated from the displacement of the surface of the artery, which is given by the integral of the velocity profile versus time. Similarly, the pressure is a function of the change in velocity of the blood versus time. In one embodiment, previously known minimum and maximum values of blood flow may be obtained via other measurements on the patient, for example via pulse transit time measurements. In another embodiment, the previously known minimum and maximum values of blood flow may be obtained from a look-up table or other reference. In one embodiment, the look-up table or other reference may be stored in memory.

Figure 6:
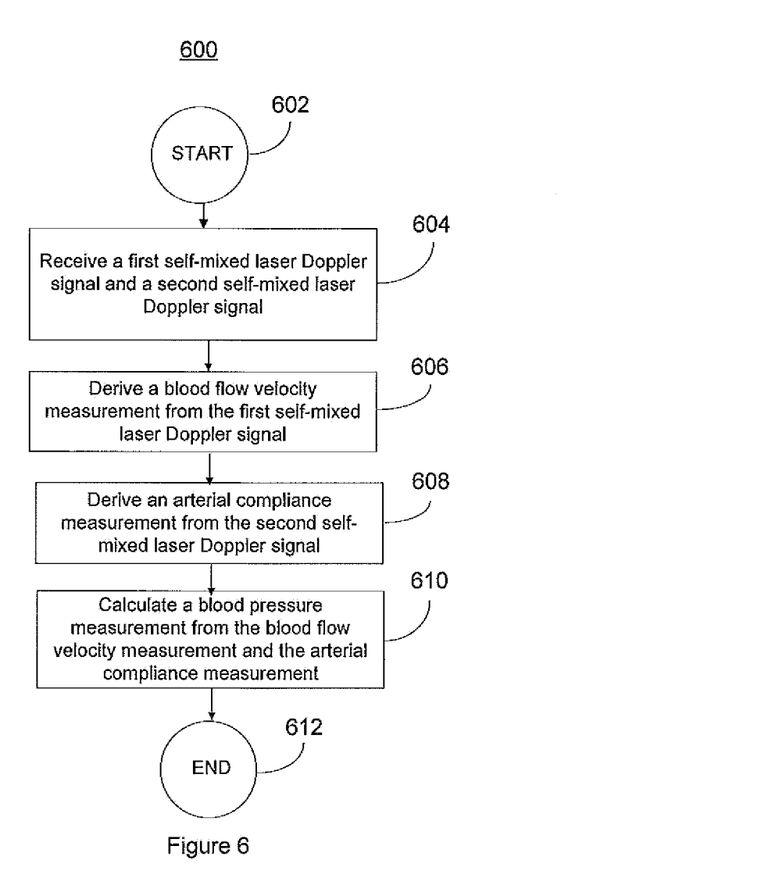
FIGS. 6 and 7 are flow charts of illustrative steps involved in the determination of blood pressure from self-mixed laser Doppler signals in accordance with an embodiment.

FIG. 6 depicts a flowchart 600 describing illustrative steps for a method of determining blood pressure via self-mixed laser Doppler measurements. The process may begin (step 602) by the appropriate placement of the laser sensors for the measurement. For example, the laser sensors may be mounted on a supporting structure 306 and placed to measure an artery of interest as depicted in FIG. 3. The process may also begin either directly after a previous blood pressure measurement has ended or some time after a previous measurement has ended. A first self-mixed laser Doppler signal and a second self-mixed laser Doppler signal are then received by the laser sensors 202 and 204 (step 604). The first self-mixed laser Doppler signal represents in part the blood flow velocity in the artery of interest, and the second self-mixed laser Doppler signal represents in part the compliance of the wall of the artery of interest. Note that the first self-mixed laser Doppler signal may also represent in part the compliance of the wall of the artery of interest, and the second self-mixed laser Doppler signal may also represent in part the blood flow velocity in the artery of interest. In step 606, a blood flow velocity measurement may then be derived in part from the first self-mixed laser Doppler signal. In one embodiment, the blood flow velocity measurement may also be derived in part from the second self-mixed laser Doppler signal. In step 608, an arterial wall compliance may be derived in part from the second self-mixed laser Doppler signal. In one embodiment, the arterial wall compliance may also be derived in part from the first self-mixed laser Doppler signal. In step 610, a blood pressure value may be calculated from the derived blood flow velocity and arterial wall compliance via the following equation:

$$V = \sqrt{\frac{tE_0}{\rho d}e^{\lambda P}} \quad (3)$$

where V, t, $E_0$, ρ, d, λ, and P are the blood flow velocity, the arterial wall thickness, the Young's modulus (which is the inverse of compliance), the density of the blood, the inner diameter of the artery, a constant of proportionality, and the blood pressure, respectively. In one embodiment, the processor 206 performs the derivation of blood flow velocity, arterial wall compliance, and blood pressure calculation. Once blood pressure is calculated, the process ends (step 612), and may be repeated again by reverting to step 602, either immediately after step 612 or after some time has elapsed. In one embodiment, the calculated blood pressure may be sent to an output 210, which may for example be a graphical display, a memory storage unit, a network, or any other means by which data may be presented, stored, or processed. In one embodiment, the calculated blood pressure may be stored in memory. In one embodiment, only one laser sensor may be used to measure either blood pressure, blood vessel compliance, or both.

Figure 7:
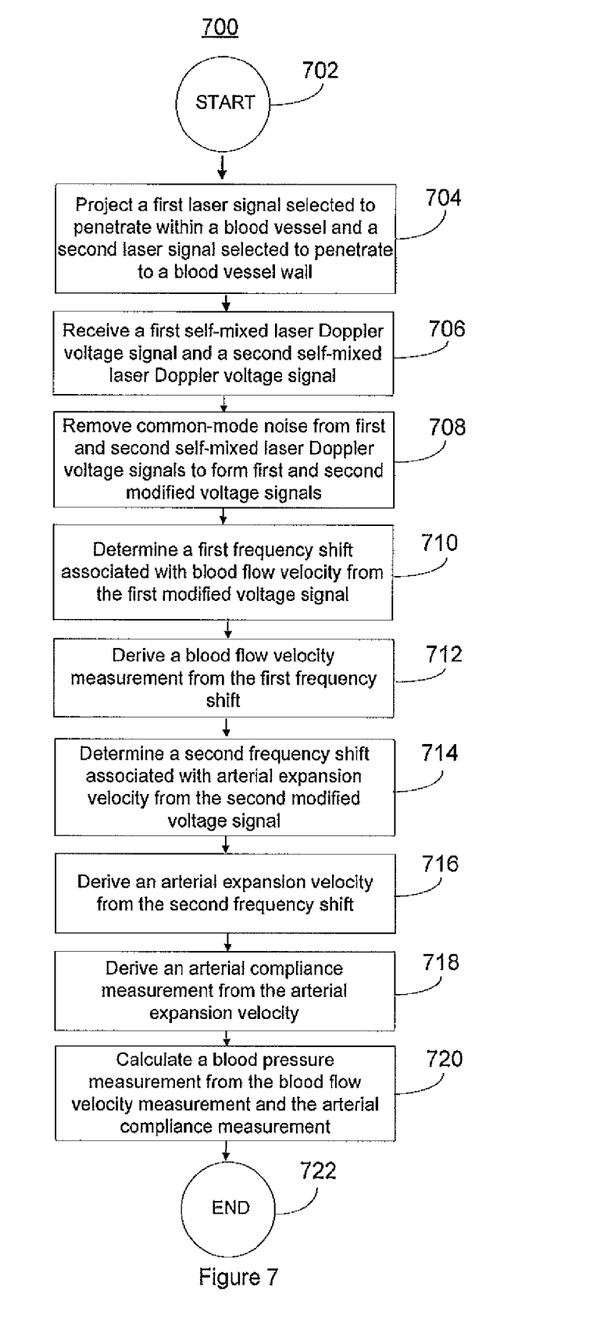

FIG. 7 depicts a more detailed flowchart 700 illustrating the steps involved in an exemplary blood pressure measurement process with self-mixed laser Doppler signals. As in flowchart 600, the process may begin (step 702) with the appropriate placement of the laser sensors or directly from the end of a previous measurement process. In step 704, a first laser signal and a second laser signal are projected into the patient. The first laser signal may be selected to penetrate within an artery, and the second laser signal may be selected to penetrate to an arterial wall but not within the artery, similar to laser signals 406 and 408. This selection may be done, for example, by selecting the wavelengths at which the first and second lasers operate. In an embodiment, the first laser signal may be in a range from 750 nm to 950 nm, which is able to penetrate deeper, and the second laser signal may be in a range from 600 nm to 850 run, which has a shallower penetration depth. In step 706, a first self-mixed laser Doppler signal and a second self-mixed laser Doppler signal is received. In step 708, the first and second laser Doppler signals may be converted to a first and second electric signal, for example by the monitor photodiode 104 present in each laser sensor. In step 710, common-mode noise may be removed from both the first and second electric signals to form a first modified electric signal and a second modified electric signal. The derivation and removal of the common-mode noise may be performed by the processor 206, for example, with a common-mode noise filter. In step 712, a first Doppler frequency shift associated with the blood flow velocity may be determined in part from the first modified electric signal. In one embodiment, the first Doppler frequency shift may also be determined in part from the second modified electric signal. The determination of the first Doppler frequency shift may be done by first converting the first modified electric signal into an amplitude versus frequency spectrum. In one embodiment, this conversion may be done by processor 206. The selection of the correct first frequency shift peak may be done as described for FIG. 5. In step 714, a blood flow measurement may be derived from the first frequency shift peak by applying equation (1), as discussed for FIG. 5. Steps 716 and 718 describe the analogous process that is performed for the second modified electric signal for the determination of arterial wall velocity. In step 716, a second Doppler frequency shift associated with the arterial wall velocity may be determined in part from the second modified electric signal via conversion into a frequency spectrum and selection of the appropriate second frequency shift peak, as described for FIG. 5. In one embodiment, the second Doppler frequency shift may also be determined in part from the first modified electric signal. In one embodiment, the conversion of the second modified electric signal and selection of the second frequency shift peak may be performed by processor 206. In step 718, the arterial wall velocity is derived from the second frequency shift peak by equation (1). In step 720, an arterial compliance may be derived from the arterial wall velocity by using equation (2). In one embodiment, the arterial compliance may be derived using a lookup table determined from clinical data. In step 721, a blood pressure value may be calculated by using equation (3) and the derived blood velocity measurement and the derived arterial compliance measurement. In one embodiment, processor 206 performs the calculation of the blood pressure measurement. Once blood pressure is calculated, the process ends (step 724), and may be repeated by reverting to step 702, either immediately after step 724 or after some time has elapsed. In one embodiment, only one laser sensor may be used to calculate blood pressure, arterial compliance, or both. In one embodiment, the calculated blood pressure may be sent to an output 210, which may for example be a graphical display, a memory storage unit, a network, or any other means by which data may be presented, stored, or processed. In one embodiment, the calculated blood pressure may be sent to a memory.

The foregoing is merely illustrative of the principles of this disclosure and various modifications can be made by those skilled in the art without departing from the scope and spirit of the disclosure. The following numbered paragraphs may also describe various aspects of this disclosure.

The invention claimed is:
1. A method for monitoring blood pressure, comprising:
receiving a first and second self-mixed laser Doppler signal, wherein the first laser signal represents at least in part a flow velocity of blood through a blood vessel and the second laser signal represents at least in part the movement of a blood vessel wall;
deriving, based at least in part on the first laser signal, the blood flow velocity;
deriving, based at least in part on the second laser signal, a compliance of the blood vessel wall; and
calculating, based at least in part on the derived flow velocity and the derived compliance, a blood pressure value using a processor.

2. The method of claim 1, wherein a first frequency shift is determined at least in part from the first self-mixed laser Doppler signal and wherein the flow velocity is determined at least in part from the first frequency shift.

3. The method of claim 1, wherein a visual or auditory signal representing the amplitude of the first self-mixed laser Doppler signal is output.

4. The method of claim 1, wherein the first and second laser signals are converted to a first and second electric signal, common-mode noise is removed from the first electric signal to form a first modified electric signal, common-mode noise is removed from the second electric signal to form a second modified electric signal, and the first and second modified electric signals are used to determine at least in part the blood flow velocity and the compliance of the blood vessel wall.

5. The method of claim 1, wherein a first frequency shift is determined at least in part from the first self-mixed laser Doppler signal and a second frequency shift is determined at least in part from the second self-mixed laser Doppler signal, and wherein the flow velocity is determined at least in part from the first frequency shift and the blood vessel wall compliance is determined at least in part from the second frequency shift.

6. The method of claim 1, wherein a visual or auditory signal representing the amplitude of the first self-mixed laser Doppler signal, the second self-mixed laser Doppler signal, or a combination of the first and second self-mixed laser Doppler signal is output.

7. A method for determining blood vessel compliance, comprising:
receiving at least two self-mixed laser Doppler signals, wherein the at least two laser signals represent at least in part the movement of a blood vessel wall and penetrate the blood vessel wall to at least two different depths, wherein the at least two laser signals represent movement of the same blood vessel; and
automatically deriving, based at least in part on the at least two laser signals, a compliance of the blood vessel wall using a processor.

8. The method of claim 7, wherein a frequency shift is determined at least in part from the at least two self-mixed laser Doppler signals, and wherein the blood vessel wall compliance is determined at least in part from, the frequency shift.

9. The method of claim 7, wherein a visual or auditory signal representing the amplitude of one of the at least two self-mixed laser Doppler signals is output.

10. A device for monitoring blood pressure, the device comprising:
a plurality of self-mixed laser sensors capable of producing at least first and second self-mixed laser signals corresponding to laser measurements; and
a processor configured to: receive the first signal and the second signal from the plurality of self-mixed laser sensors, wherein the first signal represents at least in part a flow velocity of blood through a blood vessel;
derive, based at least in part on the first signal, the blood flow velocity;
derive, based at least in part on the second laser signal, a compliance of the blood vessel wall; and
calculate, based at least in part on the derived flow velocity and the derived compliance, a blood pressure value.

11. The device of claim 10, wherein the processor is further configured to
derive at least in part a first frequency shift from the first signal; and
derive at least in part the flow velocity from the first frequency shift.

12. The device of claim 10, further comprising a notifier configured to output a visual or auditory signal representing the amplitude of the first signal.

13. The device of claim 10, further comprising:
a filter module, configured to:
remove common noise from the first signal to form a first modified signal;
remove common noise from the second signal to form a second modified signal, and
wherein the processor is further configured to determine the blood flow velocity and the compliance of the blood vessel watt based at least in part on the first and second modified signals.

14. The device of claim 10, wherein the processor is further configured to:
derive a first frequency shift at least in part from the first signal;
derive a second frequency shift at least in part from the second signal;
derive the flow velocity at least in part from the first frequency shift; and
derive the blood vessel wall compliance at least in part from the second frequency shift.

15. The device of claim 10, further comprising a notifier configured to output a visual or auditory signal representing the amplitude of the first signal, the second signal, or a combination of the first and second signals.

16. The method of claim 7, further comprising determining a blood pressure value based at least in part on the compliance.

17. A device for determining blood vessel wall compliance, the device comprising:
a plurality of self-mixed laser sensors capable of producing at least two self-mixed laser signals corresponding to laser measurements, wherein the at least two laser signals and penetrate a blood vessel wall to at least two different depths; and
a processor configured to: receive
the first and second signals, wherein the at least two laser signals represent at least in part the movement of a blood vessel wall, wherein the at least two laser signals represent movement of the same blood vessel; and
derive, based at least in part on the at least two signals, the compliance of the blood vessel wall.

18. The device of claim 17, further comprising:
a filter module, configured to:
remove common noise from one of the at east two signal to form a modified signal,
wherein the processor is further configured to determine the blood vessel compliance based at least in part on the modified signal.

19. The device of claim 17, wherein the processor is further configured to:
derive at least in part a frequency shift from one of the at least two signals; and
derive at least in part the blood vessel wall compliance from the frequency shift.

20. The device of claim 17, further comprising a notifier configured to output a visual or auditory signal representing the amplitude of one of the at least two signals.

21. The device of claim 17, wherein the processor is further configured to determine a blood pressure value based at least in part on the compliance.

22. A non-transitory computer readable medium storing computer executable instructions, which, when executed by a processor, cause the processor to carry out a method comprising:
receiving a first and second self-mixed laser Doppler signal, wherein the first laser signal represents at least in part a flow velocity of blood through a blood vessel and the second laser signal represents at least in part the movement of a blood vessel wall;
deriving, based at least in part on the first laser signal, the blood flow velocity;
deriving, based at least in part on the second laser signal, a compliance of the blood vessel wall; and
calculating, based at least in part on the derived flow velocity and the desired compliance, a blood pressure value.

23. The non-transitory computer readable medium of claim 22, wherein a first frequency shift is determined at least in part from the first self-mixed laser Doppler signal and wherein the flow velocity is determined at least in part from the first frequency shift.

24. The non-transitory computer readable medium of claim 22, wherein a visual or auditory signal representing the amplitude of the first self-mixed laser Doppler signal is output.

25. The non-transitory computer readable medium of claim 22, wherein the first and second laser signals are converted to a first and second electric signals, common-mode noise is removed from the first electric signal to form a first modified electric signal, common-mode noise is removed from the second electric signal to form a second modified, electric signal, and the first and second modified electric signals are used to determine at least in part the blood flow velocity and the compliance of the blood vessel wall.

26. The non-transitory computer readable medium of claim 22, wherein a first frequency shift is determined at least in part from the first self-mixed laser Doppler signal and a second frequency shift is determined at least in part from the second self-mixed laser Doppler signal, and wherein the flow velocity is determined at least in part from the first frequency shift and the blood vessel wall compliance is determined at least in part from the second frequency shift.

27. The non-transitory computer readable medium of claim 22, wherein a visual or auditory signal representing the amplitude of the first self-mixed laser Doppler signal, the second self-mixed laser Doppler signal, or a combination of the first and second self-mixed laser Doppler signal is output.

28. A non-transitory computer readable medium storing computer executable instructions, which, when executed by a processor, cause the processor to carry out a method comprising:
- receiving at least two self-mixed laser Doppler signals, wherein the at least two laser signals represent at least in part the movement of the blood vessel wall and penetrate the blood vessel wall to at least two different depths, wherein the at least two laser signals represent movement of the same blood vessel; and
- deriving, based at least in part on the at least two laser signals, a compliance of the blood vessel wall.

29. The computer readable medium of claim 28, wherein a frequency shift is determined at least in part from the at least two self-mixed laser Doppler signals, and wherein the blood vessel wall compliance is determined at least in part from the frequency shift.

30. The computer readable medium of claim 28, wherein a visual or auditory signal representing the amplitude of one of the at least two self-mixed laser Doppler signals is output.

31. The computer readable medium of claim 28, wherein the method further comprises determining a blood pressure value based at least in part on the compliance.

* * * * *